United States Patent
Fitzgerald et al.

(10) Patent No.: US 6,758,962 B1
(45) Date of Patent: Jul. 6, 2004

(54) OXYGEN SENSING

(75) Inventors: Matthew S. Fitzgerald, Schwenksville, PA (US); Edward C. Berdich, Downingtown, PA (US); Peter M. Draper, Honeybrook, PA (US)

(73) Assignee: Doxs Technology Systems, Inc., Downingtown, PA (US)

( * ) Notice: Subject to any disclaimer, the term of this patent is extended or adjusted under 35 U.S.C. 154(b) by 772 days.

(21) Appl. No.: 09/665,086

(22) Filed: Sep. 20, 2000

Related U.S. Application Data

(60) Provisional application No. 60/155,672, filed on Sep. 23, 1999.

(51) Int. Cl.[7] .............................. G01N 27/416
(52) U.S. Cl. .................. 205/783; 205/782; 205/782.5; 204/406; 204/431; 204/432
(58) Field of Search .............. 205/782, 782.5, 205/783; 204/406, 415, 431, 432

(56) References Cited

U.S. PATENT DOCUMENTS

| | | | |
|---|---|---|---|
| 2,861,926 A | 11/1958 | Jacobson | |
| 2,913,386 A | 11/1959 | Clark, Jr. | |
| 2,939,827 A | 6/1960 | Jacobson et al. | |
| 2,991,412 A | 7/1961 | Kordesch | |
| 3,410,778 A | 11/1968 | Krasberg | |
| 3,556,098 A | 1/1971 | Kanwisher | |
| 3,718,563 A | 2/1973 | Krull et al. | |
| 4,062,750 A | 12/1977 | Butler | |
| 4,132,616 A | 1/1979 | Tantram et al. | |
| 4,735,691 A | 4/1988 | Green et al. | |
| 5,902,467 A | 5/1999 | Wang et al. | |
| 6,099,707 A | 8/2000 | Dunigan et al. | |
| 6,303,018 B1 | * 10/2001 | Holl et al. .................. | 205/781 |

FOREIGN PATENT DOCUMENTS

| | | |
|---|---|---|
| JP | 58-153155 A | 9/1983 |
| JP | 58-200157 A | 11/1983 |
| JP | 59-26053 A | 2/1984 |

* cited by examiner

*Primary Examiner*—Kaj K. Olsen
(74) *Attorney, Agent, or Firm*—Howson and Howson

(57) ABSTRACT

Oxygen concentration measurement is carried out over a broad range by an instrument utilizing a zinc-air cell having a lower-than-nominal potential difference imposed across its electrodes by a shunt branch incorporating the source-drain circuit of a field effect transistor (FET). A feedback circuit is used to improve linearity of the output and cell life without sacrificing the broad dynamic range achieved by the use of the FET shunt branch.

9 Claims, 1 Drawing Sheet

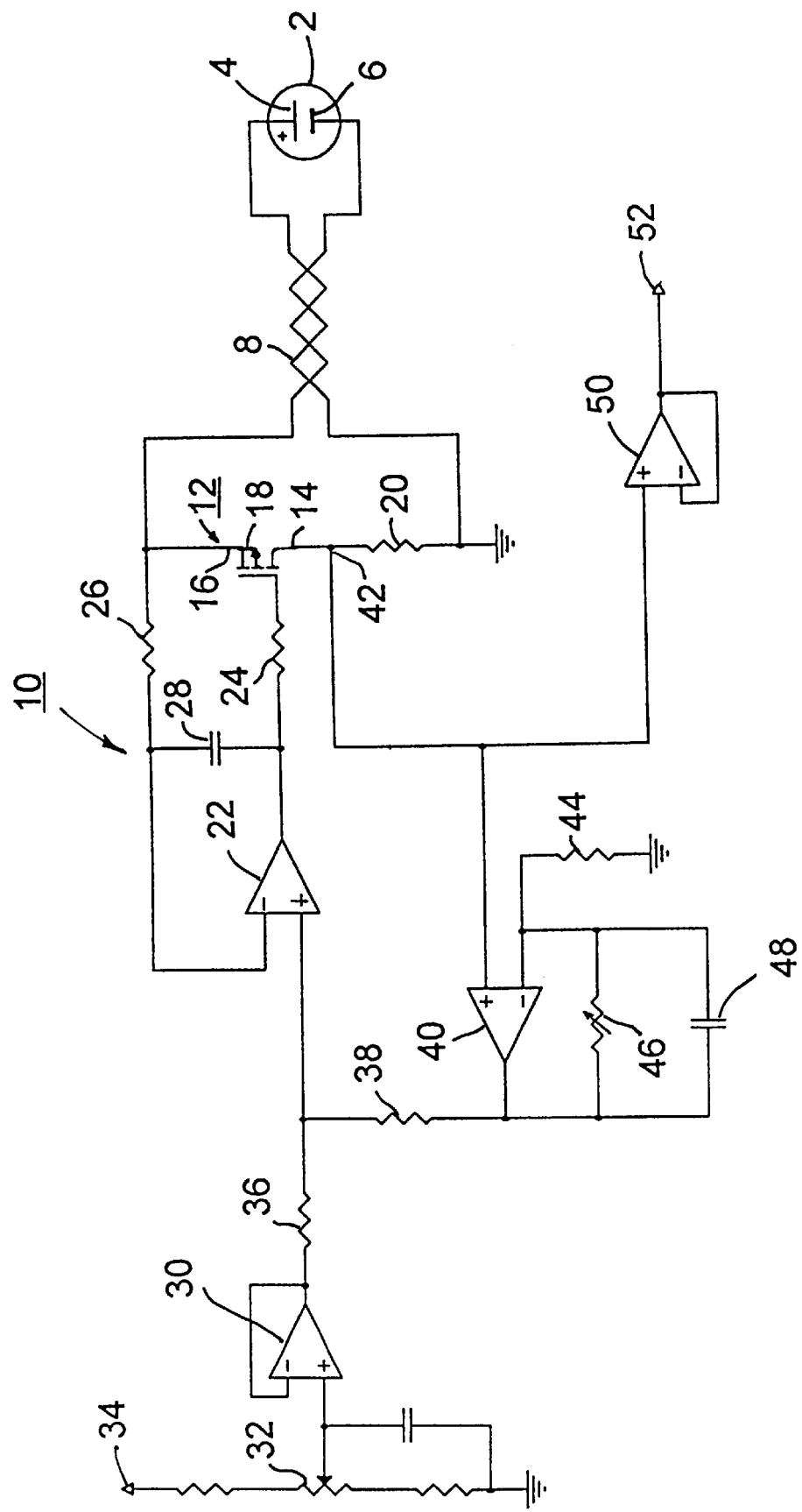

OXYGEN SENSING

CROSS-REFERENCE TO RELATED APPLICATION

This application claims priority based upon Provisional application No. 60/155,672, filed Sep. 23, 1999.

SUMMARY OF THE INVENTION

This invention relates to oxygen sensing, and more specifically to the quantitative measurement of oxygen concentration in a gaseous mixture, using a zinc-air cell. The invention has utility in a broad range of applications, including general anaesthesia in surgery, mine safety, etc.

It has been discovered that zinc-air cells, which are in common use as "hearing aid batteries," can effectively measure oxygen concentration in a gaseous mixture, and that, with appropriate circuitry, accurate quantitative measurements of oxygen concentration can be achieved over substantially the full range from 0% to 100%. In an apparatus described in U.S. Pat. No. 6,099,707, granted Aug. 8, 2000, and developed by Doxs Technology Systems, Inc. of 2090 Bondsville Road, Downingtown, Pa. 19335, the voltage across the terminals of a zinc-air oxygen sensing cell is held at a constant level, and the current in the cell is measured. With a proper choice of the constant voltage level across the cell, e.g. 0.6 volts, the current in the cell can be made to vary monotonically with oxygen concentration over the full range from 0% $O_2$ to 100% $O_2$, so that a direct meter reading of oxygen concentration can be achieved over that range.

The Doxs Technology Systems apparatus has the unique advantage that conventional zinc-air cells are relatively inexpensive and disposable. However, the Doxs apparatus also has certain disadvantages. It utilizes two operational amplifiers, one to establish a fixed voltage level at one terminal of the zinc-air cell, and the other both to maintain a fixed voltage level at the other terminal of the cell and to serve as a current-to-voltage converter, providing an output voltage proportional to the cell current. To do this, the operational amplifiers need to be able to deliver relatively high currents, and consequently consume electrical power at levels requiring large battery power supplies or frequent battery replacement.

The output current of a typical zinc-air cell varies from 0 ma. at 0% oxygen concentration to well over 90 ma. at 100% oxygen concentration. Optimization of the level of the voltage maintained across the cell for stable and accurate operation at low $O_2$ concentrations results in high cell and operational amplifier currents at high $O_2$ concentrations. Conversely, optimization of the voltage maintained across the cell for stable, accurate operation at high $O_2$ concentrations, can result in unstable and unpredictable operation at low $O_2$ concentrations, and at these low $O_2$ concentrations, operational amplifier operating current is still a concern.

Another difficulty with the prior apparatus is that, when the zinc-air cell is first installed in the measuring circuit, it produces large currents as the nominal 1.4 volt potential difference between its terminals changes to the imposed potential difference, which is typically 0.6 volts. During this time the current produced by the cell can exceed 100 ma. The circuit components capable of handling currents at this level are expensive, energy-consuming and the their power requirements are such that they are not well-suited for portable instruments. Modifications enabling the circuit to reduce the potential difference across the cell terminals from 1.4 to 0.6 volts without drawing large amounts of current introduce an excessive time delay between the installation of the zinc-air cell and the time at which the instrument is ready for operation.

Still another difficulty with the prior apparatus is that the relationship between cell current and oxygen concentration is non-linear, the current rising exponentially with increasing oxygen concentration. This makes it difficult to translate cell current to a digital output providing an $O_2$ concentration reading. It also results in a shortening of the useful life of the zinc-air cell especially when used at high oxygen concentrations.

A general object of the invention is to provide an improved apparatus for measuring oxygen concentration, which is inexpensive to manufacture and operate, which provides reliable measurements, and which is better suited for portable operation. Another object of the invention is to provide an apparatus capable of measuring oxygen concentration over a wide range but requiring only a small operating current. Another object of this invention is to provide an improved apparatus which provides stable and predictable operation over a long time. Still another object is to measure oxygen concentration over a wide range while producing an analog output signal which is a nearly linear representation of oxygen concentration, and which is therefore readily converted to digital format by an analog-to-digital converter.

The apparatus in accordance with the invention utilizes a sensor comprising a pair of sensor terminals having one or more zinc-air cells connected between them. Preferably the sensor comprises only a single zinc-air cell. Each zinc-air cell in the sensor has a pair of electrodes adapted to be exposed to a gaseous mixture in which the oxygen concentration is to be measured. The sensor is connected into a circuit for automatically maintaining the potential difference between the sensor terminals within a range below the open-circuit voltage across the sensor terminals when the sensor is exposed to air, i.e. to a gaseous mixture containing 20.9% oxygen. The circuit comprises a shunt circuit branch connected across the sensor terminals. This shunt circuit branch includes a transistor arranged to establish a controlled load on the sensor. The transistor is preferably a field-effect transistor having its source-drain circuit in the shunt circuit branch. An output circuit is connected to the sensor for delivering an electrical output signal proportional to the current in the sensor. Preferably the shunt circuit branch includes a resistor in series with the output current terminals of the transistor, i.e. the source and drain in the case of a field-effect transistor. The resistor and one of the transistor terminals are connected at a junction, and the output circuit is connected to the junction.

A control circuit, connected in driving relationship to the transistor, preferably includes means for adjusting the drive on the transistor and thereby adjusting the load on the sensor, and also preferably includes a feedback loop connected to sample the current in the sensor and to increase the potential difference between the electrodes of each cell of the sensor, by reducing the load on the sensor, as the sensor current increases, thereby increasing the linearity of the relationship between the electrical output signal and the oxygen concentration in the gaseous mixture.

The circuit, especially when utilizing a field-effect transistor as the active element of the shunt circuit branch, requires a minimum of operating current and provides an analog output varying monotonically with oxygen concentration over a wide range, which can extend from 0% to 100% oxygen. The feedback loop keeps the zinc-air cell current within its ordinary operating range, thereby yielding stable, predictable long-life operation. The feedback loop also provides an analog output which is more nearly linearly related to oxygen concentration over a wide range, simplifying conversion of the analog output signal to a digital output directly representing oxygen concentration.

Modifications can be made to the sensing cell to make it responsive to other gases such as nitrogen and carbon monoxide. Thus, although the circuit of the invention finds its principal application in the measurement of oxygen concentration, it also has application in the measurement of concentrations of such other gases.

Other objects, details and advantages of the invention will be apparent from the following detailed description when read in conjunction with the drawing.

BRIEF DESCRIPTION OF THE DRAWING

The single FIGURE is a schematic diagram showing a preferred oxygen concentration measurement circuit in accordance with the invention.

DETAILED DESCRIPTION

Referring to the FIGURE, a zinc-air cell 2 has its electrodes 4 and 6 connected, through a twisted two-wire cable 8, to a circuit 10.

The zinc-air cell 2 can be an ordinary 600 milliampere-hour hearing aid cell such as a Varta 675 cell. The zinc-air cell comprises a zinc anode inside a casing having one or more apertures (not shown) for the entry of a gaseous mixture into the interior of the casing. The zinc anode is covered by a series of layers (not shown). These include a separator/barrier layer, a current collector layer and a catalytic layer where a cathode reactor occurs A gas-permeable membrane (not shown) is provided inside the casing to control the passage of the gaseous mixture into contact with the catalytic layer. The sizes of the apertures are selected to provide the cell with the desired response time. The nominal output voltage of the cell is 1.4 volts, when exposed to ordinary air, i.e. air containing 20.9% oxygen.

The circuit branch 12 is connected in shunt with the zinc-air cell. This shunt branch comprises the source and drain terminals, 16 and 14 respectively, of an insulated gate field effect transistor (FET) 18, connected in series with a resistor 20, which preferably has a low resistance, e.g. 1.0 ohm.

The gate of the FET 18 is driven by an operational amplifier 22 through a resistor 24. The "−" input of the operational amplifier is connected to the source 16 of FET 18 through a resistor 26. A capacitor 28, connected from the output to the "−" input of the operational amplifier, cooperates with resistor 26 to provide a filter to prevent oscillation. The "+" input of the operational amplifier 22 receives an input from another operational amplifier 30. The level of this input is established by an adjustable resistor 32 connected in a series of resistors between a positive supply terminal 34 and ground.

Resistors 36 and 38 serve as an adding circuit, combining the output of operational amplifier 30 with the output of still another operational amplifier 40, which is part of a feedback loop. The "+" input of operational amplifier 40 is connected directly to a junction 42 between the drain 14 of FET 18 and resistor 20. The "−" input of operational amplifier 40 is connected to ground through resistor 44 and to the output of the operational amplifier 40 through resistor 46. The resistor 46 can be fixed or adjustable. Here as in the case of amplifier 22, a capacitor 48 is provided to prevent oscillation. As an alternative, the "−" input of operational amplifier 40 could be connected to a circuit similar to the circuit connected to the "+" input of operational amplifier 30.

The junction 42 between the drain 14 of FET 18 and resistor 20 is also connected to the "+" input of a fourth operational amplifier 50, which delivers its output to an output terminal 52. The output of the operational amplifier 50 is connected directly to its "−" input.

In the operation of the circuit described above, the adjustable resistor 32 is set so that the shunt branch 12 holds the potential difference between the electrodes of the zinc-air cell 2 at a level below the nominal 1.4 volt level which corresponds to the open-circuit voltage of the cell when exposed to ordinary air, i.e. air containing 20.9% oxygen. Preferably, with the cell exposed to ordinary air, the potential difference between the cell electrodes is set to approximately 1.2 volts, i.e. slightly less than the nominal open circuit cell voltage. When the potential between the electrodes is held at 1.2 volts, the current in the cell, and consequently the voltage appearing across resistor 20, will vary monotonically with oxygen concentration over the entire range from 0% to 100% oxygen. That is, the cell current increases with increasing oxygen concentration, and for every value of oxygen concentration throughout the range from 0% to 100%, there is a unique corresponding value of cell current, and therefore a unique output voltage at terminal 52. In this regard, the performance of the device in accordance with this invention is similar to that of the prior Doxs Technology Systems oxygen sensing apparatus except that the new device draws a significantly lower operating current.

In the device shown, the level of the voltage imposed on the electrodes of the zinc-air cell is controlled not only by the setting of adjustable resistor 32, but is also controlled by the feedback loop incorporating operational amplifier 40. As cell current increases with increasing oxygen concentration, the feedback signal increases, reducing the drive on FET 16 and increasing the potential difference impressed upon the electrodes of the zinc-air cell. With the potential difference maintained at a constant level of 1.2 volts, the cell current would range from 0 ma at 0% $O_2$, through about 1 ma at 20.9% $O_2$, to about 40 ma at 100% $O_2$. With the feedback circuit in operation, the cell current still ranges from 0 ma at 0% $O_2$, through about 1 ma at 20.9% $O_2$. However, the potential difference imposed on the cell is continuously increased as cell current increases. At the high end of the oxygen concentration range, i.e. 100% $O_2$, the potential difference can be 1.35 volts, and the corresponding current can be only about 4 ma, well below the level at which it would be without the feedback circuit. The output voltage at terminal 52 is more nearly linear and more easily converted to a digital representation of oxygen concentration. The current drain on the zinc-air cell is also substantially lower, and consequently the zinc-air cell has a longer useful life, and the oxygen concentration measurements are repeatable and reliable. It is important that the feedback circuit achieves the advantages of better linearity, improved cell life and more reliable measurements while still allowing the apparatus to measure oxygen concentration over the full oxygen concentration range from 0% to 100%.

Various modifications can be made to the apparatus described. For example, instead of using an adjustable resistor 32 to control set the drive level for FET 12 in the shunt branch, the "+" input of amplifier 30 can be controlled, through a digital-to-analog converter, by a microprocessor which is part of a computer-controlled oxygen sensing system incorporating zinc-air cell, the shunt branch utilizing and FET, and the feedback loop. All four operational amplifiers can be on the same chip as components of a single integrated circuit. Transistors other than FETs can be used in the shunt branch, and the feedback and output signals can be derived across the same element or across separate elements at various locations in the mesh comprising the zinc-air cell and the source-drain circuit of the transistor. For example, with appropriate circuit modifications, the ground connection to resistor 20 and junction 42 can be interchanged. Although it has been found that the results achievable with a single zinc-air cell are entirely satisfactory, it is possible to utilize multiple zinc-air cells, in series, in parallel, or in a hybrid arrangement, to form a single oxygen sensing cell.

Finally, even though it is normally desirable to impose a potential difference across the zinc-air cell such that measurements of oxygen concentration can be taken over the full range from 0% to 100% $O_2$, it is possible to realize some of the advantages of the invention in an instrument in which the potential difference imposed across the cell permits effective readings of oxygen concentration over less than the full range. For example, in applications where oxygen concentration will always exceed 50%, the voltage imposed across the cell can be higher than 1.2 volts. Accurate and reliable readings and good linearity can be achieved in the measurement of relatively high oxygen concentrations, even though good readings at low concentrations may not be possible.

Although the embodiment depicted in the drawing utilizes a P-channel field effect transistor, it is possible to utilize an N-channel field effect transistor instead, making the appropriate reversal of the connections to the inverting and non-inverting inputs of operational amplifier 22.

Of course, various modifications other than those specifically mentioned above may be made to the apparatus and method described above without departing from the scope of the invention as defined in the following claims.

What is claimed is:

1. An apparatus for measuring the concentration of a gas in a gaseous mixture comprising:
    a sensor comprising a pair of sensor terminals having at least one zinc-air cell connected between them, each zinc-air cell in the sensor having a pair of electrodes adapted to be exposed to the gaseous mixture when the sensor is exposed to the gaseous mixture;
    a circuit for automatically maintaining the potential difference between the sensor terminals within a range below the open-circuit voltage across the sensor terminals when the sensor is exposed to air, the circuit comprising a shunt circuit branch connected across the sensor terminals, the circuit branch including a transistor arranged to establish a controlled load on the sensor; and
    an output circuit connected to the sensor for delivering an electrical output signal proportional to the current in the sensor.

2. An apparatus according to claim 1 in which the sensor consists of a single zinc-air cell having its electrodes connected respectively to the sensor terminals.

3. An apparatus according to claim 1, in which the transistor is a field-effect transistor having its source-drain circuit in the shunt circuit branch.

4. An apparatus according to claim 1, in which two terminals of the transistor are in the shunt circuit branch, in which the shunt circuit branch includes a resistor in series with said two terminals of the transistor, in which the resistor and one of said transistor terminals are connected at a junction, and in which the output circuit is connected to said junction.

5. An apparatus according to claim 1, in which the transistor is a field-effect transistor having its source-drain circuit in the shunt circuit branch, and in which the shunt circuit branch includes a resistor in series with the source-drain circuit of the transistor, in which the resistor and the source-drain circuit are connected at a junction, and in which the output circuit is connected to said junction.

6. An apparatus according to claim 1, including a control circuit connected in driving relationship to the transistor, the control circuit including means for adjusting the drive on the transistor and thereby adjusting the load on the sensor.

7. An apparatus according to claim 1, including a control circuit connected in driving relationship to the transistor, the control circuit including a feedback loop connected to sample the current in the sensor and to increase the potential difference between the electrodes of each cell of the sensor, by reducing the load on the sensor as the sensor current increases, thereby increasing the linearity of the relationship between said electrical output signal and the concentration of said gas in the gaseous mixture.

8. An apparatus according to claim 1, including a control circuit connected in driving relationship to the transistor, the control circuit including:
    means for adjusting the drive on the transistor and thereby adjusting the load on the sensor; and
    a feedback loop connected to sample the current in the sensor and to increase the potential difference between the electrodes of each cell of the sensor, by reducing the load on the sensor as the sensor current increases, thereby increasing the linearity of the relationship between said electrical output signal and the concentration of said gas in the gaseous mixture.

9. A method for measuring the concentration of a gas in a gaseous mixture comprising:
    exposing, to the gaseous mixture, a sensor comprising a pair of sensor terminals having at least one zinc-air cell connected between them, each zinc-air cell in the sensor having a pair of electrodes exposed to the gaseous mixture;
    imposing a controlled load on the sensor by a shunt circuit branch including a transistor, thereby automatically maintaining the potential difference between the sensor terminals within a range below the open-circuit voltage across the sensor terminals when the sensor is exposed to air; and
    deriving from the sensor an electrical output signal proportional to the current in the sensor; and determining the concentration of the gas from the electrical output signal.

* * * * *